United States Patent
Mardi et al.

(10) Patent No.: US 9,284,251 B2
(45) Date of Patent: Mar. 15, 2016

(54) COMPLEX ZINC AND ALPHA-CHLOROCARBOXYLIC ACID COMPOUNDS FOR TREATING SKIN LESIONS

(75) Inventors: Shalva Iosifovitch Mardi, Binninden (CH); Lev Aleksandrovich Ustynyuk, Moscow (RU)

(73) Assignee: Obschestvo S Ogranitchennoi Otvetstvennostju "OXYGON", Moscow (RU)

( * ) Notice: Subject to any disclaimer, the term of this patent is extended or adjusted under 35 U.S.C. 154(b) by 184 days.

(21) Appl. No.: 14/232,226

(22) PCT Filed: Nov. 14, 2011

(86) PCT No.: PCT/RU2011/000896
§ 371 (c)(1),
(2), (4) Date: Feb. 25, 2014

(87) PCT Pub. No.: WO2013/022369
PCT Pub. Date: Feb. 14, 2013

(65) Prior Publication Data
US 2014/0171501 A1 Jun. 19, 2014
US 2015/0141504 A9 May 21, 2015

(30) Foreign Application Priority Data

Aug. 5, 2011 (RU) ................................ 2011132922

(51) Int. Cl.
*C07C 53/19* (2006.01)
*A61K 31/315* (2006.01)
*C07C 53/16* (2006.01)
*C07F 3/06* (2006.01)

(52) U.S. Cl.
CPC ............... *C07C 53/19* (2013.01); *A61K 31/315* (2013.01); *C07C 53/16* (2013.01); *C07F 3/06* (2013.01)

(58) Field of Classification Search
CPC ...... C07C 53/19; C07C 53/16; A61K 31/315; C07F 3/06
See application file for complete search history.

(56) References Cited

U.S. PATENT DOCUMENTS

| 4,595,591 | A  | 6/1986  | Mardi et al. ................... 424/127 |
| 6,558,694 | B2 | 5/2003  | Brooks et al. ................. 424/443 |
| 7,128,903 | B2 | 10/2006 | Burstein .................. 424/195.11 |
| 7,258,875 | B2 | 8/2007  | Chiou ........................... 424/617 |
| 2009/0054252 | A1 | 2/2009 | Lanzendoerfer et al. ......... 506/9 |
| 2011/0052641 | A1 | 3/2011 | Mardi et al. ................. 424/277.1 |
| 2013/0149395 | A1 | 6/2013 | Mardi et al. ................... 424/401 |

FOREIGN PATENT DOCUMENTS

| EP | 1437124 | 7/2004 |
| EP | 1746082 | 1/2007 |
| RU | 2014830 | 6/1994 |
| RU | 2261243 | 9/2005 |
| RU | 2366648 | 9/2009 |
| RU | 2375054 | 12/2009 |
| RU | 2375054 C2 * | 12/2009 |

OTHER PUBLICATIONS

Zelenak et al. "Thermal Properties of Zinc(II) Chloroacetate and Its Complexes With Nicotinamide and Caffeine" Journal of Thermal Analysis, 1996, vol. 46, pp. 573-579.*
Letter/Written Disclosure of the Supplemental Information Disclosure Statement for the above-referenced application, filed herewith on Nov. 19, 2015, 2 pages.
Certified English translation of RU2014830, published Jun. 20, 2014, entitled: "Face Skin Cream," 5 pages.
Letter/Written Disclosure of the Information Disclosure Statement for the above-referenced application, mailed Jun. 30, 2014, 2 pages.
Berezin, B., "Reactivity of transition metal solvates," Russ Chem Rev., 60(9):996-1007 (1991) and translated from the Russian language found in: Uspekhi Khimii, 60:1946-1968 (1991).
Chen et al., "A novel two-dimensional chiral coordination polymer: bis(S-(−)-lactate)zinc(II)," Inorg Chem Comm., 3(9):493-496 (2000).
Certified English translation of EP 1437124B1, published Mar. 26, 2008, entitled: "Composition for the treatment of acne," 7 pages.
Certified English translation of RU 2366648C2, published Oct. 9, 2009, entitled: "Reaction product of selenium dioxide and ali phatic haloid carboxylic acids, method for making product, solution of product and therapy of benign, virus, premalignant and malignant nonmetastasing skinn affections, dysontogenetic lesions of visible mucous membranes and other skin diseases," 36 pages.
Certified English translation of RU 2375054C2, published Oct. 12, 2009, entitled: "Preparation for treatment of skin affections, method for making said preparartion (versions) and method of treating skin affections," 57 pages.

(Continued)

*Primary Examiner* — Joseph Kosack
(74) *Attorney, Agent, or Firm* — Dentons US LLP; Stephanie Seidman

(57) ABSTRACT

The invention relates to the field of medicine, and specifically to preparations for treating skin lesions, in particular viral, benign, precancerous and cancerous, non-metastasizing, dysplastic and inflammatory lesions of the visible mucous membranes, and also viral and fungal skin and nail lesions, and for correcting wrinkles and senile pigment blemishes, said preparations comprising solutions of complex compounds of salts of zinc and alpha-chlorocarboxylic acids of general formula $[Zn(RCH_{2-x}Cl_xCOOH)_n(H_2O)_{4-n}]^{+2} \cdot 2[RCH_{2-x}Cl_xCOO]^-$, where R=alkyl, H or Cl, x=1-2 and n=0-4, in a corresponding alpha-chlorocarboxylic acid, wherein the content of zinc in the solution is 0.25-10.0% and the content of acid is 10-90%. The preparation may additionally contain an additive perfume, for example an ethyl ester of the corresponding alpha-chlorocarboxylic acid. The treatment method consists in that 2-5 doses of the preparation, which has been precooled to 10-15° C., are applied to the affected skin portion with a delay of 1-3 mins between the first and subsequent applications of the preparation. The preparations are stable on storage.

17 Claims, No Drawings

(56) References Cited

OTHER PUBLICATIONS

Goldschmied et al., "The crystal structure of ZnII propionate (C6H10O4Zn)n," Acta Chrystallogr., Sect. B. Struct. Crystallogr. Cryst. Chem., 33(Pt 7):2117-2120 (1977).
Lacouture et al., "Anhydrous polymeric zinc(II) octanoate," Acta Chrystallogr., Sect. B. Struct. Crystallogr. Cryst. Chem., 56(Pt 5):556-557 (2000).

International Search Report, mailed Apr. 26, 2012, in connection with International Patent Application No. PCT/RU2001/000896 [English translation], 1 page.
Written Opinion, mailed Apr. 26, 2012, in connection with International Patent Application No. PCT/RU2001/000896 [English translation], 4 pages.
International Preliminary Report on Patentability, issued Feb. 11, 2014, in connection with International Patent Application No. PCT/RU2001/000896 [English translation], 5 pages.

* cited by examiner

COMPLEX ZINC AND ALPHA-CHLOROCARBOXYLIC ACID COMPOUNDS FOR TREATING SKIN LESIONS

RELATED APPLICATIONS

This application is the National Stage of International Application. No. PCT/RU2011/000896, filed 14 Nov. 2011, which claims benefit of priority to Russian Patent Application No. RU 2011132922, filed 5 Aug. 2011, the specification of which is incorporated by reference herein.

The present invention relates to medicine, and, in particular, to the field of pharmaceutical drugs intended for the treatment of tumors and other lesions of skin and mucous membranes. It concerns both a composition for acid necrosis of tumor tissues and mucous membranes and its preparation and application method.

Skin diseases are dramatically widespread and present a great variety of forms (pyodermatites, cutaneous mycoses, virus dermatoses, parasitic dermatosis, infectious dermatoses, dermatoses of various aetiology, tumors, etc.). Skin mostly suffers from bad environmental conditions and viscus diseases, thus revealing the general state of health of an individual. Skin abnormalities exhibit a wide range of sizes, shapes, colors, penetration depths, etc., though they do not always pose a threat to a patient.

Skin tumors require special consideration, as the majority of them should be surgically removed. Capable of growing large, benign tumors may interfere with the normal functioning of other organs and systems and become malignant under adverse conditions, which is the reason for their being dangerous. Many skin lesions do not exhibit any signs of malignization, therefore they are not usually biopsied and are rather treated via cryosurgery, laser therapy and electrocoagulation. However, these methods often cause discomfort to patients such as pain, inflammations, edemata and haematomas. The recovering process is slow and, with a wound left open for spontaneous healing, the process is sometimes accompanied by a secondary infection, which requires a post-operative antibiotics therapy. Being an alternative way of treating a tumor, application of cytostatics has a serious shortcoming as it involves normal cells of the lesion as well, which is not the main target. The most radical treatment is a surgical extraction of all the abnormal cells of a new growth including a deep and surrounding portion of sound tissue.

Different pharmaceutical compositions based on inorganic and organic acids and their salts are widely and rather successfully used to treat many skin diseases. As new data on the action mechanism of certain chemical elements, their biological role and ways of metabolism in an organism as well as cell growth and development peculiarities of benign and malignant tumors is reported, the amount of patent information in this sphere gradually increases. As to inorganic acids, nitric acid (less often hydrochloric acid) is commonly used, and as to organic acids, carbolic, acetic, trichloracetic, salicylic and other acids are commonly used.

Substances and compositions capable of inducing acid necrosis in contact with tissues and mucous membranes are designated as "caustic agents" (less often as "corrosive agents", "necrotizing agents" or "disruptive agents"), whereas the acids are called "keratolytic" acids. The acids are considered to induce dehydration and subsequent cell death through the mechanism of necrosis.

Acid-based compositions are in demand due to their relative simplicity, accessibility and effectiveness of application. A great number of improvements mostly concern the selection of "softer" acids and their combinations with common antimicrobials and anti-inflammatory drugs, including herbal raw material extracts containing alkaloids. There is no registration data on the majority of these compositions applied as medications.

Zinc compounds have long been used for treating skin diseases and keeping skin healthy and have proved to show good results. Back in the middle of the last century, it was F. Mohs who determined that zinc chloride is able to fix cells that undergo a chemically induced necrosis, which makes histopathological tissue examination possible during the treatment. Recently an improved zinc chloride based paste containing the vegetable alkaloid sanguinarine has been invented for treating melanomas and skin tumors using Mohs' chemosurgery method (U.S. Pat. No. 6,558,694, 2003. Brooks N. A., Brooks L. S., Zinc chloride unit dose packaging, applicator, and method of use in treating cancer and other skin diseases). The alkaloid acts like an antibacterial, antifungal and antiprotozoal remedy, and is produced in the form of an aqueous-alcoholic solution or pills by the Russian Pharmcenter VILAR company, as an example.

A mixture of trichloracetic, hydrochloric and formic acids with zinc chloride (U.S. Pat. No. 7,128,903, 2001. Burstein P., Pharmaceutical preparations useful for treating tumor and lesions of the skin and the mucous membranes and methods and kits using same), a mixture of zinc, copper and cadmium salts with salicylic acid (U.S. Pat. No. 7,258,875, 2007. Chiou Win L., Compositions and methods for topical treatment of skin infection), a mixture of zinc and copper salts with organic oxoacid (EP 1 437 124 B1, 2004. Marion C., Composition for the treatment of acne) and some other compositions have been invented for treating skin diseases.

However, medical experts do not consider the majority of these compositions as reliable medications, since there are often no results of clinical trials registered and the effect is not clear yet. The evaluation of these compositions' effectiveness as a skin disease treatment shows that a high recovery rate is observed only in patients with tumors graded Level I or II by Clark and Breslow scales. Tumors graded from III to V levels by Clark and Breslow scales can hardly be treated without the risk of recurrences, though the increase of life-expectancy is evident.

The prototype of the present invention is described in RU 2 261 243 C1, wherein zinc salts and halide carboxylic acids of the general formula $(RCOO)_2Zn$, where $R=CHal_3$, $CHHal_2$, $CH_2Hal$, or $(R''CH_2CHR'COO)_2Zn$, where R' and $R''=H$, Hal, or alkyl have been proposed as the active substances (RU Pat. No. 2 261 243, 2004. Sh. Mardi, A. F. Tsib, L. I. Krikunova, Zinc and haloid carboxylic acids salts of aliphatic series for skin and visible mucous membrane neoplasms treatment). Based on these studies, drugs have been developed (RU Pat. No. 2 375 054 C2, 2007. Sh. Mardi, A. F. Tsib, Pharmaceutical preparation for skin lesions treatment, obtaining method (alternatives) and skin lesions treatment method).

The results of extensive application proved these pharmaceutical compositions to be highly effective. However, while storing the substance for a long time, precipitation was observed, which required further research.

The principal object of the present invention is the elimination of detected shortcomings and the development of methods for safe and effective tumor chemical necrosis using cauterizing agents, capable of chemical necrosis of the target-tissue depthward without affecting healthy tissue areas, where necrosis should be avoided.

The only limitation for the new formulation development concerned the minimal change of the prototype composition regarding the inclusion of adjuvants without officinal classification.

The object is attained by the invention of a new composition with better consumer attributes by application of new coordination compounds of zinc salts and halide carboxylic acids as active substances and by eliminating typical "acid" smell to minimize the psychological discomfort caused to patients.

The object is attained by the complex of zinc salts and alpha-chlorocarboxylic acid compounds with the general formula $[Zn(RCH_{2-x}Cl_xCOOH)_n(H_2O)_{4-n}]^{+2}.2[RCH_{2-x}Cl_x COO]^-$, wherein R=alkyl, H or Cl, x=1-2, and n=0-4.

In particular, the complex compound may be a complex compound of a Zn-alpha-chloropropionate and alpha-chloropropionic acid of the general formula $[Zn(CH_3CHClCOOH)_n(H_2O)_{4-n}]^{+2}.2[CH_3CHClCOO]^-$, where n=0-4.

The object is attained by the pharmaceutical composition for treating skin lesions, and, in particular, viral, benign, premalignant, and malignant non-metastasizing skin lesions, dysplastic (pre-tumor) and inflammatory lesions of visible mucous membranes as well as virus and fungous nail and skin lesions, for wrinkles and senile nevus pigmentosus correction by acid necrosis, wherein said pharmaceutical composition is a solution of the coordination compound of the general formula $[Zn(RCH_{2-x}Cl_xCOOH)_n(H_2O)_{4-n}]^{+2}.2[RCH_{2-x}Cl_x COO]^-$, wherein R=alkyl, H or Cl, x=1-2, and n=0-4 in a halide carboxylic acid $RCH_{2-x}Cl_xCOOH$.

In particular, this pharmaceutical composition is a solution of the coordination compound of Zn-alpha-chloropropionate and alpha-chloropropionic acid of the general formula $[Zn(CH_3CHClCOOH)_n(H_2O)_{4-n}]^{+2}.2[CH_3CHClCOO]^-$, wherein n=0-4.

The pharmaceutical composition for treating skin lesions further comprises an odorant in the amount of from 0.1 to 1.0% by weight.

The odorant may be the appropriate ethyl chlorocarboxylate.

The object is attained by the method of preparation of the pharmaceutical composition for treating skin lesions, wherein the coordination compound of the general formula $[Zn(RCH_{2-x}Cl_xCOOH)_n(H_2O)_{4-n}]^{+2} 2[RCH_{2-x}Cl_xCOO]^-$ is dissolved in alpha-chlorocarboxylic acid of the general formula $RCH_{2-x}Cl_xCOOH$, wherein R=alkyl, H or Cl, x=1-2, and n=0-4 and the total amount of zinc and acid in the solution is from 0.25 to 10.0% by weight and from 10 to 90.0% by weight, respectively.

In particular, this coordination compound of the general formula $[Zn(RCH_{2-x}Cl_xCOOH)_n(H_2O)_{4-n}]^{+2}.2[RCH_{2-x}Cl_x COO]^-$ may be the coordination compound of a Zn-alpha-chloropropionate and alpha-chloropropionic acid of the general formula $[Zn(CH_3CHClCOOH)_n(H_2O)_{4-n}]^{+2}.2 [CH_3CHClCOO]^-$, wherein n=0-4, that is dissolved in 2-chloropropionic acid, wherein the total amount of zinc and acid in the solution is from 0.25 to 10.0% by weight and from 10 to 90.0% by weight, respectively.

The object is attained also by the method of treating skin lesions, wherein the pharmaceutical composition pre-cooled to 10-15° C. is applied to the treated lesion area in 2-5 steps, with 1-3 min. exposure between the first and subsequent applications.

The chemical and spectral analysis of precipitates forming from the solution after a long-term storage of the substance proved that they conform of the general formula $Zn(CH_3CHClCOO)_2.CH_3CHClCOOH.H_2O$ and are solvated complexes of the general formula

$[Zn(CH_3CHClCOOH)_n(H_2O)_{4-n}]^{+2}.2[CH_3CHClCOO]^-$.

IR spectrums of solvate samples contain intensive absorption bands at 1625, 1408 and 1368 cm$^{-1}$, that correspond to the stretching vibrations of the C=O group, and two absorption bands at 3543 and 2994 cm$^{-1}$, corresponding to the stretching vibrations of the O—H group of carboxylic acids respectively. The characteristic frequency shift of the C=O group into the long-wave range is typical of molecular complexes, comparing with monomers of carboxylic acids (1790 cm$^{-1}$) and their dimers (1720-1700 cm$^{-1}$). The comparison with spectrums of propionic acid cesium salt (Aldrich Catalog No 33379-4, CAS No 38869-24-8) and 4-hydroxybutanoic acid sodium salt (Aldrich Catalog No H2222-1, CAS No 502-85-2) proves the reference of the absorption bands.

The structure was additionally proved by the analysis of recognized theoretical data, concerning X-ray diffraction of zinc salts of carboxylic acids, which showed that zinc atoms of one salt molecule are coordinatively bound with the carbonyl group of the other molecule in the crystal cell unit (E. Goldschmied, A. D. Rae, N. C. Stephenson, 1977. Acta Chrystallogr., Sect. B. Struct. Crystallogr. Cryst. Chem., pp 33, 2117—propionate. F. Lacouture, J. Peultier, M. Francois, J. Steinmetz, 2000, Acta Chrystallogr., Sect. B. Struct. Crystallogr. Cryst. Chem., pp 56, 556—octanoate. Zhen-Feng Chen, Jing Zhang, Ren-Gen Xiong, Xiao-Zeng You, 2000, Inorg. Chem. Commun., pp 3, 493—zinc lactate).

Solvates have been proved to exist in solutions by a number of experiments. Stability peculiarities of coordination spheres of transition metal salt solvates and, in particular, acid salts ($MX_n^{n-2}$) and acid solvate salts ($MX_2S_{n-2}$) have been examined in Berezin's review (Berezin B. D., 1991, "Reactivity of transition metal solvates", Uspekhi Khimii, vol. 60, pp 1946-1968).

They are considered to be the result of a weak intermolecular interaction, but in some cases their chemical bond strength makes it difficult to distinguish them from chemical compounds. For instance, having very strong chemical bonds, hydrates of some zinc salts form crystallohydrates when the solution is concentrated. Crystallohydrates, such as $ZnSO_4.7H_2O$ or $Zn(NO_3)_2.6H_2O$, retain water even when heated at more than 100° C. Other crystallohydrates, for instance, $Zn(CH_3COO)_2.2H_2O$, dehydrate even when slightly heated, whereas $ZnCl_2.1.5H_2O$ is stable only at a temperature lower than 26° C. (Angelov I. I., Karyakin Y. V., 1974, "Pure chemical substances", Khimia, Moscow, pp 397-403).

The $Zn^{+2}$ ion is known as a strong complexing compound. Most of the $Zn^{+2}$ salts have a coordination number 4, much more rarely 6 or 8. Capable of interacting with lone-electron pairs of water molecules, $Zn^{+2}$ ions form aqua complexes with formula $[Zn(H_2O)_4]^{+2}$ or $[Zn(H_2O)_6]^{+2}$. With anions such as $Cl^-$-ions present in a solution, a considerable part of the water molecules might be replaced by a chloride ion and form the compounds $[Zn(H_2O)_2Cl_2]$, $[Zn(H_2O)_2Cl_3]^-$ and the like. The latter competes with the solvent structure, thus revealing non-linear concentration and temperature dependence of solution viscosity, density and electrical conductivity.

The isolated precipitates are colorless solids characterized by no distinct melting point. The level of zinc concentration reveals their close relation to compounds $(CH_3CHClCOO)_2 Zn.2CH_3CHClCOOH.H_2O$ or $(CH_3CHClCOO)_2 Zn.2CH_3CHClCOOH.2H_2O$. They are stable only in contact with the liquid phase. When kept in the open air or slightly heated, the zinc and acid concentrations in the solvates change, the number of molecules in the complex coordination sphere decreases and the hydrated ion becomes less complex.

Unlike zinc salts of chlorocarboxylic acids described in the prototype patent, the solvated complexes of the general formula $[Zn(CH_3CHClCOOH)_n(H_2O)_{4-n}]^{+2}.2[CH_3CHClCOO]^-$ dissolve even in low polar organic solvents, especially with small amounts of water present.

The obtained compounds were subsequently used for synthesis of substance and dosage forms. Their stability was tested in real storage conditions and by applying an accelerated aging method.

It was proved that the substance solutions prepared on the basis of solvated complexes remained stable during the whole expiration period, whereas the solutions prepared according to RU 2 261 243 C1 and to RU 2 375 054 C2 were stable only at an acid concentration of 80% and lower.

Increases in acid or salt concentration in the solution and higher temperatures lead to a decrease in the solubility of the complexes. Density of zinc-2-chloropropionate solutions in 2-chloropropionic acid is characterized by non-linear concentration and temperature dependence.

It should be noted that the chemical composition of solvate precipitates forming from the solutions differ from those of the solvates in the solution. Therefore it is impossible to rely on the precipitate chemical composition in identifying the composition of the solvates in the solution.

It is preferable to use solvates obtained by interaction of ZnO with alpha-chlorocarboxylic acid at a reagent ratio of 1:30-1:40. In that case solutions of the compositions are more stable than the solutions obtained at a reagent ratio of 1:1 (as in the prototype).

Another advantage of the present invention is the formation of a very thin glossy film on the skin surface after the application of the composition, which indicates the low speed of penetration of a solvated complex into the skin. Unexpectedly, this feature lessened acid necrosis side effects such as reddening or edema, almost eliminated the pain and accelerated natural skin color restoration.

In order to prevent contact with healthy skin areas, the composition is preferably cooled to 10-15° C. before applying it to a tumor.

Typical "acid" smell is easily eliminated by adding into the composition small amounts of odorants such as ethyl esters of the corresponding acids.

Bacteriological research shows that the solutions prepared in accordance with the present invention are sterile and free of pathogenic flora.

EXEMPLARY EMBODIMENTS

Example 1

Preparation of $[Zn(CH_3CHClCOOH)_n(H_2O)_{4-n}]^{+2}.2[CH_3CHClCOO]^-$, Substance and Dosage Forms on its Basis 10.85 g (0.1 g/mol) of 2-chloropropionic acid (98.0% purity) were added to a suspension consisting of 0.51 g (0.0063 g/mol) of zinc oxide in 5 ml of water and were stirred with a magnetic stir bar at 20-25° C. until the precipitate had been completely dissolved. The stirring was subsequently continued for 1.5-2.0 hours. Then, the preparation included dropwise addition of 97.65 g (0.9 g/mol) of the acid, with every new portion added only after the precipitate had been dissolved. The stirring was continued for another 30 min., until 114 g of a substance solution had been obtained, with 1.26 g/cm³ density and the zinc and 2-chloropropionic acid concentration of 4.55 mg/ml and 1.19 g/ml, respectively.

Diluting the substance with water produced a dosage form with the acid concentration of about 50% (the composition 1-1), characterized by 1.15 g/cm³ density and the zinc and 2-chloropropionic acid concentration of 2.3 mg/ml and 0.58 g/ml, respectively.

1.0% ethyl 2-chloropropionate was included in the composition 1-1, thereby obtaining the composition 1-2.

Example 2

Preparation of $[Zn(CH_3CCl_2COOH)_n(H_2O)_{4-n}]^{+2}.2[CH_3CCl_2COO]^-$, Substance and Dosage Forms on its Basis 14.3 g (0.1 g/mol) of 2,2-dichloropropionic acid (98.7% purity) were added to a suspension consisting of 0.51 g (0.0063 g/mol) of zinc oxide in 5 ml of water and stirred with a magnetic stir bar at 20-25° C. until the precipitate had been completely dissolved. The stirring was subsequently continued for 2.0-2.5 hours. Then, the preparation included dropwise addition of 128.7 g (0.9 g/mol) of the acid, with every new portion added only after the precipitate had been dissolved.

148.0 g of a solution were obtained, with 1.4 g/cm³ density and the zinc and 2,2-chloropropionic acid concentration of 3.8 mg/ml and 1.33 g/ml, respectively.

Diluting the substance with water produced a 50% solution (the composition 2-1) with the acid concentration of 0.6 g/ml and the zinc concentration of 1.85 gm/ml.

0.5% by weight of ethyl 2,2-dichloropropionate was included in the composition 2-1, thereby obtaining the composition 2-2.

Example 3

Preparation of $[Zn(CCl_3COOH)_n(H_2O)_{4-n}]^{+2}.2[CCl_3COO]^-$ and dosage Forms on its Basis 16.353 g (0.1 g/mol) of trichloroacetic acid (98.7% purity) were added to a suspension consisting of 0.51 g (0.0063 g/mol) of zinc oxide in 5 ml of water and stirred with a magnetic stir bar at 20-25° C. until the precipitate had been completely dissolved. The stirring was subsequently continued for 1.5-2.0 hours. Then, the preparation included dropwise addition of 147.15 g (0.9 g/mol) of the acid in 55 ml of water, with every new portion added only after the precipitate had been dissolved.

184.0 g of a 70% trichloroacetic acid solution were obtained, with 1.08 g/cm³ density, the zinc concentration of 1.87 g/ml and the 2,2-dichloropropionic acid concentration of 0.75 gm/ml (the composition 3-1).

0.1% by weight of ethyl trichloroacetate was included in the composition 3-1, thereby obtaining the composition 3-2.

Example 4

Preparation of $[Zn(CHCl_2COOH)_n(H_2O)_{4-n}]^{+2}.2[CHCl_2COO]$, Substance and Dosage Forms on its Basis 12.9 g (0.1 g/mol) of dichloroacetic acid (95% purity) were added to a suspension consisting of 0.51 g (0.0063 g/mol) of zinc oxide in 5 ml of water and stirred with a magnetic stir bar at 20-25° C. until the precipitate had been completely dissolved. The stirring was subsequently continued for 2.0-2.5 hours. Then, the preparation included dropwise addition of 116.1 g (0.9 g/mol) of the acid, with every new portion added only after the precipitate had been dissolved.

134.0 g of a solution were obtained, with 1.52 g/cm$^3$ density, the zinc concentration of 4.1 g/ml and the dichloroacetic acid concentration of 1.43 gm/ml.

Diluting the substance with water produced a 50% solution (the composition 4-1) with the acid concentration of 0.7 g/ml and the zinc concentration of 2.0 gm/ml.

1.0% ethyl dichloroacetate was included in the composition 4-1, thereby obtaining the composition 4-2.

Corroboration of Actual Reduction

Example 1

A 46 year old woman (patient A) complained of a slowly growing mole on her breast. The medical examination revealed a brown oval pappilomatous mass with a 2.5×2.0 cm wide base, no pain on palpation. The biopsy diagnosed an intradermal melanocytic nevus. The composition 1-1 was applied in two doses, each of 0.1 mg, with a three-minute interval. In 20 minutes the treated lesion area took on a gray-yellow color, and a thin strip of hyperemic skin appeared around the tumor. In 24 hours the nevus turned black and mummified. On the 30$^{th}$ day after the application the mummified tissue spontaneously separated from the dermis. In 60 days natural skin color restoration occurred on the application spot. During the subsequent 12 months there were neither pathological changes of the nevus area, nor complaints. The treatment was successful.

15 patients diagnosed with epidermal nevus, junction melanocytic nevus, mixed melanocytic nevus, halo nevus and verrucous melanocytic nevus were similarly treated.

Example 2

A 77 year old man (patient M) complained of a verruca plana on his left cheekbone. The medical examination revealed a 4.2×3.5 cm yellowish brown irregular mass protruding 2-3 mm above the skin surface. The biopsy result, the dermatologist and the pathologist diagnosed seborrheic keratosis. The composition 1-2 was applied five times to the lesion area with a two-minute-interval, for a total dosage of 0.2 mg. In 10 minutes after the application the treated lesion area took on a gray color, with a thin strip of hypermia and a slight edema around it. The skin altered by keratosis turned black and mummified in 24 hours. In 28 days there were still hyperkeratotic thickenings under separated mummified scabs; therefore the repeated single dose application of 0.1 ml was performed. A mild hyperemic spot was noted at the seborrheic keratoma area in 30 days after the repeated application. There were neither pathological changes on the skin at the seborrheic keratosis area, nor complaints during the follow-up. The treatment was successful.

7 patients diagnosed with actinic and benign lichenoid keratosis were similarly treated.

Example 3

A 74 year old woman (patient V) complained of a gradually growing tumor that appeared about two years ago in the parietal area. The biopsy, the dermatologist and the pathologist diagnosed cutaneous horn. The composition 2-1 was applied five times to the lesion area with a 1-2 minute interval, for a total dosage of 0.15 mg. In 10 minutes the tumor surface took on a yellow-gray color, with a slight skin edema and a strip of hyperemia around it. In 24 hours the tumor surface turned black and mummified. In 45 days the mummified scabs of the tumor spontaneously separated from the dermis. There were no pathological changes on the skin at the cutaneous horn area during the follow-up. The treatment was successful.

Example 4

A 36 year old woman (patient D) complained of warts on the skin of both hands. The medical examination revealed numerous dense rounded epidermal papulae with a rough pale pink surface, 1.0-4.0 mm in diameter. After the biopsy, the dermatologist and the pathologist diagnosed common warts. The composition 2-2 was applied three times to the lesion area with a 1.5-2 minute interval, for a total dosage of 0.2 mg. In 10 minutes the warts' surfaces took on a yellowish-gray color. In 24 hours the warts turned black and mummified. In 22-28 days the mummified scabs of the warts spontaneously separated from the dermis. Hyperemic spots of the same size as their bases were noted at the warts' area within 30 days after the application. The natural skin color restoration on the application spot occurred on the 60$^{th}$ day. There were neither pathological changes on the skin at the area of the warts, nor relapse during the follow-up. The treatment was successful.

12-patients diagnosed with common, flat or plantar warts were similarly treated.

Example 5

A 62 year old woman (patient C) complained of slowly growing nodes that appeared 3 years ago on her forearms and shanks. The medical examination revealed more than a dozen slightly pigmented flat papulae, 0.1-0.7 in diameter. After the biopsy, the dermatologist and the pathologist diagnosed numerous large cell acanthomas. The composition 3-1 was applied three times to all the nodes with a 1.5-2 minute interval, for a total dosage of 0.15 mg. In 10-15 minutes after the application the nodes surface took on a yellow-gray color, with a slight skin edema and a strip of hyperemia around it. In 24 hours the nodes turned black and mummified. In 25-35 days the mummified scabs of the nodes spontaneously separated from the dermis. There were hyperemic and heightened pigmentation spots at the area of the nodes for some time, but they completely disappeared in 2 months after the application. There were neither pathological changes on the skin at the area of the nodes, nor relapse during the follow-up.

Example 6

A 76 year old woman (patient A) complained of multitude wrinkles on her face that couldn't be resolved with the help of cosmetic agents. The dermatologist diagnosed face wrinkles. According to the medical data and the patient's choice, it was decided to carry out a deep face peel. After receiving the patient's consent, the composition 3-2 was applied twice to the excessively wrinkled skin areas with a 1-1.5 minute-interval with the help of a cotton swab for a total dosage of 2.0 mg. In 10 minutes the face skin took on a light-yellow color, and in 24 hours superficial epidermis mummification was noted. In 7-9 days the mummified epidermis scabs spontaneously separated from the dermis. In 3 weeks after the application the majority of small wrinkles on the patient's face skin diminished; on some areas, viz. cheeks, they completely disappeared. There were no pathological changes on the skin after the peel during the follow-up.

Example 7

A 57 year old man (patient K) complained of itching red weeping maculae between toes as well as nail destruction and lamination on the first and the second toes. The patient had been examined by a dermatologist who diagnosed foot skin moniliasis, but the treatment had no effect. The medical examination confirmed the diagnosis. The microscopic scrapes study of the skin lesion areas revealed fungus druses. The dermatologist diagnosed foot skin moniliasis with subungual lesion. The composition 4-1 was applied three times to the lesion area with a 1.5-2 minute interval, for a total dosage of 0.15 mg. In 10-15 minutes the treated skin areas took on a yellow color, with a slight edema and a hyperemia around it. In 24 hours the treated skin areas darkened and mummified. In 14-16 days after the application the mummified areas spontaneously separated from the dermis. In 2-3 months, complete nail shape and color restoration were noted. There was no moniliasis relapse during the follow-up. The treatment was successful.

What is claimed is:

1. Coordination compounds of zinc salts and alpha-chlorocarboxylic acids of the general formula:

$$[Zn(RCH_{2-x}Cl_xCOOH)_n(H_2O)_{4-n}]^{+2} \cdot 2[RCH_{2-x}Cl_xCOO]^-,$$

wherein:
R=alkyl, H or Cl;
x=1-2; and
n=1-4.

2. The coordination compounds of claim 1, wherein the coordination compounds are coordination compounds of zinc salt and alpha-chloro-propionic acid of the general formula:

$$[Zn(CH_3CHClCOOH)_n(H_2O)_{4-n}]^{+2} \cdot 2[CH_3CHClCOO]^-,$$

wherein n=1-4.

3. A pharmaceutical composition, comprising
the coordination compound of claim 1
in a halide carboxylic acid of formula $RCH_{2-x}Cl_xCOOH$, wherein:
R=alkyl, H or Cl; and
x=1-2.

4. The pharmaceutical composition of claim 3, wherein the pharmaceutical composition is a solution of the coordination compound of zinc salt and alpha-chloropropionic acid of the general formula $$[Zn(CH_3CHClCOOH)_n(H_2O)_{4-n}]^{+2} \cdot 2[CH_3CHClCOO]^-, \text{ wherein } n=1\text{-}4.$$

5. The pharmaceutical composition of claim 3, further comprising an odorant in an amount of from 0.1 to 1.0% by weight.

6. The pharmaceutical composition of claim 5, wherein the odorant is an ethyl ester of the corresponding chlorocarboxylic acid.

7. A method of preparation of a pharmaceutical composition for treating skin lesions, comprising:
dissolving the coordination compound of claim 1
in an alpha-chlorocarboxylic acid of the general formula
$RCH_{2-x}Cl_xCOOH$, wherein R=alkyl, H or Cl, x=1-2, and n=1-4,
wherein the total amount of zinc and acid in the solution is from 0.25 to 10.0% by weight and from 10 to 90.0% by weight, respectively.

8. The method of claim 7, wherein the coordination compound of Zn-alpha-chloropropionate and alpha-chloropropionic acid of the general formula $$[Zn(CH_3CHClCOOH)_n(H_2O)_{4-n}]^{+2} \cdot 2[CH_3CHClCOO]^-, \text{ wherein } n=1\text{-}4,$$

is dissolved in 2-chloropropionic acid, wherein the total amount of zinc and acid in the solution is from 0.25 to 10.0% by weight and from 10 to 90.0% by weight, respectively.

9. A method of treating skin lesions, comprising:
cooling the pharmaceutical composition of claim 3 to 10-15° C.; and
applying the cooled composition to the lesion area in 2-5 applications, with a 1-3 min. interval between the first and subsequent applications.

10. The pharmaceutical composition of claim 4, further comprising an odorant in an amount of from 0.1 to 1.0% by weight.

11. The pharmaceutical composition of claim 10, wherein the odorant is an ethyl ester of the corresponding chlorocarboxylic acid.

12. A method of treating skin lesions, comprising:
cooling the pharmaceutical composition of claim 4 to 10-15° C.; and
applying the cooled composition to the lesion area in 2-5 applications, with a 1-3 min. interval between the first and subsequent applications.

13. The method of claim 9, wherein the skin lesion is selected from among viral, benign, premalignant, and malignant non-metastasizing skin lesions, dysplastic (pre-tumor) and inflammatory lesions of visible mucous membranes, and viral and fungal nail and skin lesions.

14. A method of treating wrinkles, comprising:
cooling the pharmaceutical composition of claim 3 to 10-15° C.; and
applying the cooled composition to the area containing wrinkles in 2-5 applications, with a 1-3 min. interval between the first and subsequent applications.

15. A method of treating senile nevus pigmentosis, comprising:
cooling the pharmaceutical composition of claim 3 to 10-15° C.; and
applying the cooled composition to the pigmented area in 2-5 applications, with a 1-3 min. interval between the first and subsequent applications.

16. The coordination compounds of claim 1 of a zinc salt and dichloroacetic acid of the general formula:

$$[Zn(CHCl_2COOH)_n(H_2O)_{4-n}]^{+2} \cdot 2[CHCl_2COO]^-,$$
wherein n=1-4.

17. The coordination compounds of claim 1 of a zinc salt and trichloroacetic acid of the general formula:

$$[Zn(CCl_3COOH)_n(H_2O)_{4-n}]^{+2} \cdot 2[CCl_3COO]^-,$$
wherein n=1-4.

* * * * *